United States Patent [19]

Shahid

[11] Patent Number: 5,768,335
[45] Date of Patent: Jun. 16, 1998

[54] APPARATUS AND METHOD FOR MEASURING THE ORIENTATION OF A SINGLE CRYSTAL SURFACE

[75] Inventor: Muhammed Afzal Shahid, Ewing Township, N.J.

[73] Assignee: Lucent Technologies Inc., Murray Hill, N.J.

[21] Appl. No.: 798,580

[22] Filed: Feb. 10, 1997

[51] Int. Cl.$^6$ .................................................. G01N 23/207
[52] U.S. Cl. ................................................ 378/73; 378/71
[58] Field of Search .................................. 378/73, 71

[56] References Cited

U.S. PATENT DOCUMENTS 5,187,729  2/1993  Ibe et al. .................................... 378/73

OTHER PUBLICATIONS

Duane O. Townley, *Optimum Crystallographic Orientation For Silicon Device Fabrication*, Solid State Technology, pp. 43–47, Jan. 1973.

Kurt E. Petersen, *Silicon as a Mechanical Material*, Proceedings of the IEEE, vol. 70, No. 5, pp. 420–457, May 1982.

Brian Tuck, *Review –The Chemical Polishing of Semiconductors*, Journal of Materials Science 10, pp. 321–339, 1975.

*Primary Examiner*—Craig E. Church

[57] ABSTRACT

An apparatus and method for measuring the misorientation of a polished surface of a single crystal wafer with respect to a set of low index crystal planes utilizes both an optical beam and an X-ray beam that are directed along the same axis at the wafer. The optical beam is reflected by the polished surface of the wafer, but the X-ray beam penetrates the surface and is diffracted by the low index crystal planes located below the surface. The separation between the diffracted and reflected beams is measured with a detection device. The separation between the reflected and diffracted beams is an indication of the magnitude and sense of the misorientation between the surface and the crystal planes.

26 Claims, 4 Drawing Sheets

APPARATUS AND METHOD FOR MEASURING THE ORIENTATION OF A SINGLE CRYSTAL SURFACE

FIELD OF THE INVENTION

The apparatus and method of the present invention relates to the processing of a monocrystalline substrate, and more particularly an apparatus and method for measuring the orientation of the surface of the substrate with respect to one or more low index planes.

BACKGROUND OF THE INVENTION

Monocrystalline substrates, such as silicon wafers, typically comprise the building blocks of most microelectronic devices. In practice, silicon wafer manufacturers dice wafers from a single crystal ingot such that each wafer has its upper surface slightly tilted, or misoriented by a magnitude often approximately 3 degrees. The direction, or sense of the tilt from the wafer's vicinal or true (100) crystal plane is often along either the (0$\bar{1}$1) or (01$\bar{1}$) plane after polishing. Those skilled in the art have discovered that in many cases, purposely misorienting the polished surface of the wafer enhances and improves subsequent wafer oxidation processes and other surface deposition steps.

While purposely misorienting the polished surface of a wafer often improves many semiconductor processes for fiber optic devices, misorientation above certain magnitudes may create problems in optical fiber alignments. In the case of V-grooves precisely formed in a monocrystalline wafer by anisotropic etching, substantial misorientation of the V-grooves relative to a low index crystal plane may lead to misalignment of one or more of the optical fibers held by the assembly. This problem has been described and addressed in commonly owned U.S. patent application Ser. No. 08/408,800 filed Mar. 23, 1995.

As a result of the positive and negative impacts of wafer surface misorientation, those skilled in the art have realized the importance of, and need for, screening of individual wafers for appropriate surface orientations for particular applications. This involves measuring the surface orientations before allowing subsequent processing. Failure to do so may result in the costly scrapping of fully fabricated but defective fiber optic components.

A variety of conventional techniques exist for establishing the crystallographic orientation of the wafer. One such technique involves chemical etching of the wafer surface to produce etch-pits, whereby the shape of the etch-pits is usually indicative of the wafer orientation. One proposal, by Townley, is discussed in "*Optimum Crystallographic Orientation For Silicon Device Fabrication*", Solid State Technology, Jan. 1993 (pp. 43–47). (See also, "*The Chemical Polishing Of Semiconductors*", Journal of Materials Science, 1975 (pp. 321–339); "*Silicon As A Mechanical Material*", Proceedings of the IEEE, May 1982 (pp. 420–457). These technologies utilize visible light reflected from the etched surface of the wafer to produce a set of detectable lobes having a prescribed size relationship with each other depending upon the orientation of the wafer. Unfortunately, the etching of the wafer destroys the wafer for all practical purposes, thereby characterizing this procedure as destructive. Because of the costs involved in physically destroying the structures, wafers used in the orientation measurement are typically taken from stock already removed from production as defective for any number of reasons. The individual wafer is traceable to the particular originating ingot such that wafers from the same lot may be identified as having the particular measured orientation. While this method works well for its intended purposes, by destructively testing defective wafers the accuracy of the resulting orientation measurement becomes subject to a plurality of unknown variables.

Another conventional method for determining surface orientation involves using X-rays, as proposed by Laue, see chapter 8 of *Elements of X-ray Diffraction*, B.D. Cullety (Addison Wesler 1956). In the Laue method, X-rays are directed to the surface of the crystal and reflected therefrom. The reflected X-rays follow a path to a sheet of photographic film to expose a complex image representing the crystal surface orientation. After the film develops, skilled technicians interpret the exposed image to determine the orientation information. Although this method avoids destruction of the wafer, the time and labor involved to extract the orientation information from the film makes such a process undesirable in automated high production environments. Moreover, because of the "indirect" manner of taking an X-ray diffraction pattern, the predictability and accuracy of the surface orientation of the test wafer are only approximate.

Therefore, those skilled in the art have realized the need for an apparatus and method for accurately measuring the orientation of a monocrystalline substrate surface without destroying the substrate and which is applicable for use in automated high speed production operations. The apparatus and method of the present invention satisfy these needs.

SUMMARY OF THE INVENTION

The apparatus and method of my present invention conveniently provide nondestructive measurements of monocrystalline substrates to determine the orientations of the substrates and their surfaces. By directly measuring the substrate surface orientation, my invention offers a substantially higher degree of accuracy than indirect measuring means and methods. As a result, the costs involved in proceeding with the full fabrication of semiconductor devices from wafers that were initially defective due to misorientation, can be substantially minimized.

The method of the present invention comprises a technique for measuring the misorientation of a polished surface of an immobilized crystal substrate with respect to a set of low index crystal planes of the crystal which exists beneath the polished surface. The method includes the steps of establishing a reference beam of radiation (e.g. x-ray radiation) along a predetermined path to non-destructively penetrate the surface and diffract from the set of crystal planes at a predictable angle to define a diffraction beam; and guiding an optical (e.g. light) beam along the predetermined path co-linear with the reference beam of radiation to reflect from the surface of the substrate. If there is misorientation between the polished surface and the crystal plane, there will be a relative separation between the position of the diffraction radiation beam and the reflected optical beam which is directly related to the misorientation.

To realize the advantages of this method, the apparatus of my present invention comprises a beam detection device for use with a measurement system having an energy beam source (e.g. an X-ray source), an optical beam source (e.g. a light source), and a substrate fixture. The detection device includes a multi-axis platform and a scale mounted on the platform. The platform includes a track formed along a track path disposed radially equidistant from a predetermined point. A multi-detector mechanism is mounted slidably to the track and includes respective energy beam and light beam detectors disposed in measurably adjustable relative relation along the track.

During use, as the energy and optical beams are directed towards the substrate located at the predetermined point, the energy beam will diffract from the crystal plane and the optical beam will reflect from the substrate surface. The detectors are moved along the track to allow them to align with the respective diffracted and reflected beams. The aligned detectors define a relative spacing therebetween corresponding to the relative angular separation between the respective beams, which represents the sense and magnitude of misorientation of the substrate surface with respect to its vicinal low index crystal plane.

BRIEF DESCRIPTION OF THE DRAWINGS

The foregoing and other features and advantages of the present invention will be more readily apparent from the following detailed description when read in conjunction with the accompanying drawings, wherein.

DETAILED DESCRIPTION OF THE PREFERRED EMBODIMENTS

Figure 1A:
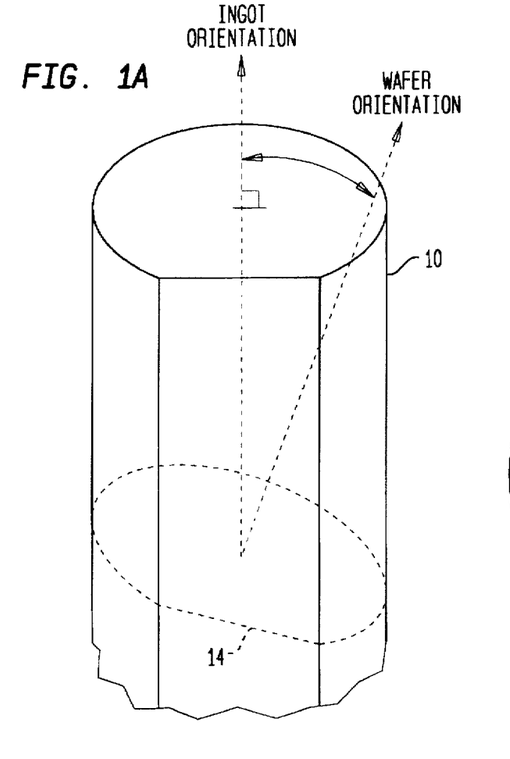
FIG. 1A is an elevated partial perspective view of a monocrystalline ingot and showing a cutting plane.
Figure 1B:
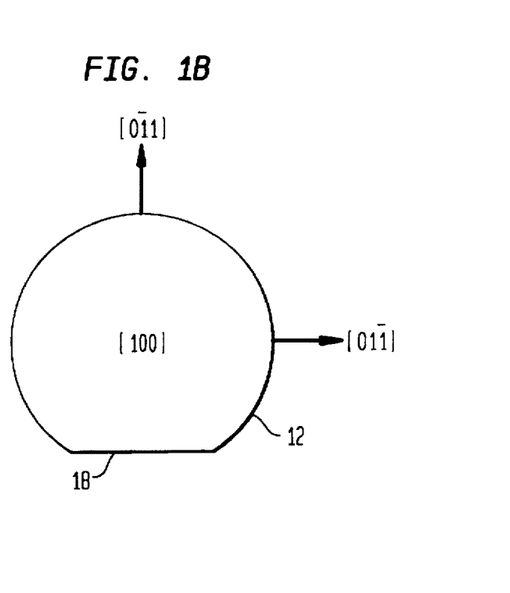
FIG. 1B is a top plan view of a monocrystalline wafer diced from the ingot of FIG. 1A.

In practice, wafers of the type used in the microelectronic and opto-electronic industries, such as Si, Ge, ZnS, GaAs, InP, CdTe, to name a few, are diced from a single crystal ingot 10, as shown in FIG. 1A. The cuts are made such that each wafer 12, such as shown in FIG. 1B, has its upper surface 14 slightly tilted (typically about 3 degrees) from the wafer's vicinal or true (100) crystal plane along either the (0 $\bar{1}$1) or (01$\bar{1}$) plane after polishing. Low index crystalline planes 16, (FIGS. 2A and 2B) underlying the polished surface 14 are aligned in parallel stacked relation according to the vicinal plane. Accurately aligning the surface 14 at the proper angle with respect to the planes 16 facilitates improved control over wafer oxidation methods and other surface deposition steps performed during the processing of the wafer.

With reference to FIG. 1B, during processing, a reference flat 18 is ground into the wafer 12 parallel to the [01$\bar{1}$] direction. Although all wafer manufacturers grind one or two flats in each wafer, there is no standard regarding the orientation of the flat. For different manufacturers, the flat may be oriented differently. Further, it should be pointed out that unlike Si and Ge, the [0$\bar{1}$1] and [01$\bar{1}$] directions in III–V (GaAs, InP, and others) and II–VI semiconductors (Cd Te, ZnS, and others) are not equivalent. Thus, it is typically not possible to determine the orientation of the wafer, and more particularly, the orientation of the tilt axis, simply by reference to the location of the reference flat 18.

Referring to FIG. 2A, it should be understood that processing of the monocrystalline wafer surface during wafer fabrication typically involves purposely misorienting, or tilting, the polished wafer surface 14 with respect to the plurality of vicinal low index parallel crystalline planes 16. In order to measure the magnitude and sense of the surface misorientation, one must be able to determine the relative angle θ between the vector n (normal to the polished surface 14), and the vector ghkl (normal to the low index crystalline planes 16).

It has long been known that if an X-ray beam, such as Xo, is directed at a polished substrate surface, the beam will propagate through the surface and, at a suitable angle which is determined by the Bragg condition, the beam will diffract off of one of the crystalline planes to form a diffraction beam, such as X'. Under such conditions, the angle of the diffracted beam will equal the angle of the incident beam and comprise a predictable reference beam representing the orientation of the low index vicinal plane 16. As is well known in the art, not every low index crystal plane satisfies the Bragg condition.

While an X-ray beam comprises radiation capable of non-destructively passing through the polished wafer surface 14, optical radiation cannot. Instead, an optical beam, such as 0, reflects from the polished surface at a reflection angle, and is directed towards O'. I have discovered that when both beams are initially incident on the same point P on the substrate 12 (FIGS. 2A, 2B and 3), the angular relationship between a Bragg diffracted X-ray beam, X', and a reflected optical beam, O', is 2θ. Therefore, by measuring this relationship, the misorientation, θθ, of the crystal surface 14 with respect to the vicinal plane 16 can be easily calculated.

Figure 3:
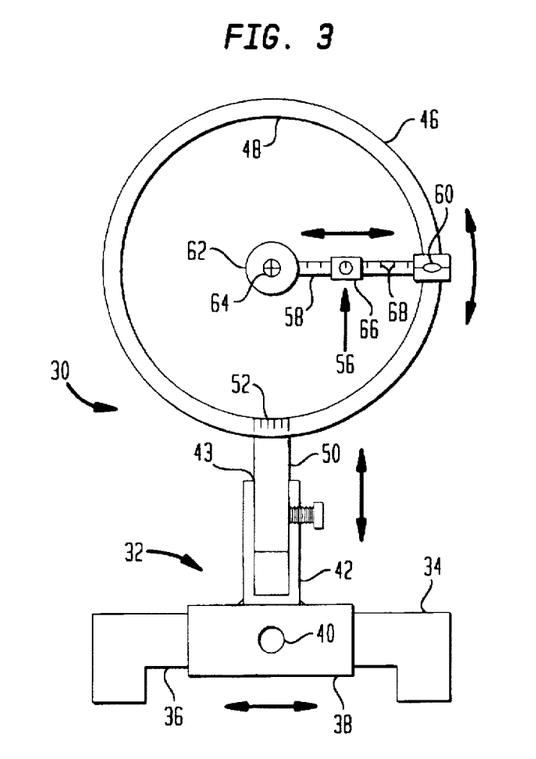
FIG. 3 is a block diagram illustrating one embodiment of a system for carrying out the principles of the present invention.
Figure 4A:
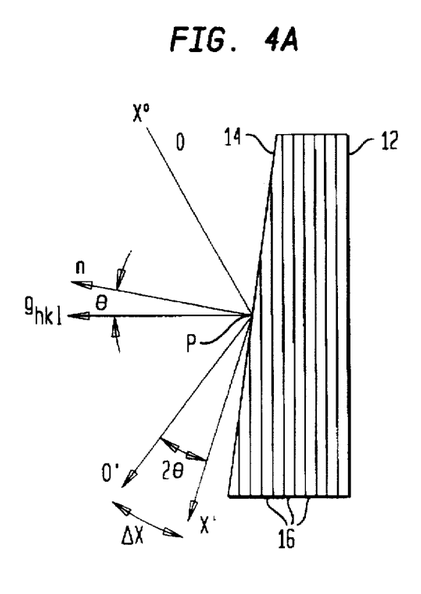
FIG. 4 is a detailed rear view of a detection device which can be utilized as one embodiment of the apparatus of FIG. 3.
Figure 4B:
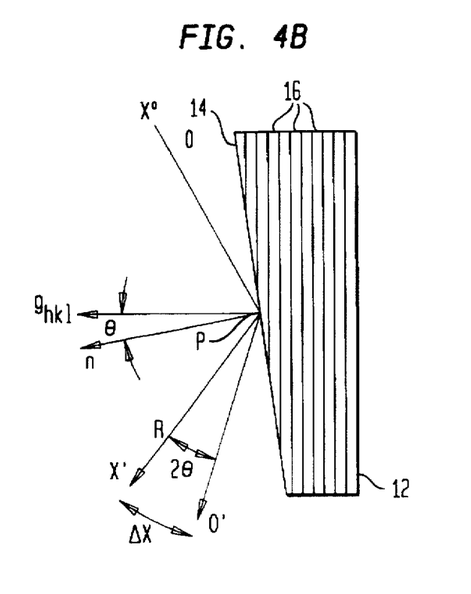

FIGS. 3 and 4, show apparatus for implementing the concepts of the invention, i.e. the measurement of the magnitude and sense of the orientation of the surface 14 with respect to the planes 16. According to this embodiment of the present invention, a measurement system 20 includes an energy beam source 22, an optical beam source 26, a substrate fixture 28, and a detection device 30.

The energy beam source 22 typically comprises an X-ray source which produces an X-ray beam Xo (FIGS. 2A and 2B) along a controllable path 24 in the direction of the wafer 12 so as to non-destructively penetrate the polished surface 14 of the wafer 12 and diffract off a lower index plane 16 to form a diffracted beam X'(see FIGS. 2A and 2B). It is anticipated that other sources of radiation capable of penetrating the polished surface such as electron beams and ion beams, may be utilized in place of the X-ray beam.

An important consideration in the energy source used involves the nondestructiveness and predictability of the diffracted energy beam. In the case of X-rays, by satisfying the Bragg condition, as is well known in the art, the angle of diffraction from the set of low index planes will equal the angle of incidence. In this manner, the diffracted beam X' serves as a convenient reference beam for marking the relative orientation of the lower index plane 16.

The optical beam source 26 typically comprises any form of visible, infrared or ultraviolet light beam source capable of directing a light beam O (FIGS. 2A and 2B) along the same path 24 taken by the energy beam Xo. However, unlike the surface penetrating characteristic of the beam from the energy source 22, the key consideration for the optical radiation implemented by the optical beam involves its ability to reflect off the misoriented polished surface 14 to form a reflected beam O'. In the case of a surface misoriented wafer, O' will be displaced relative to the diffracted beam X'.

Further referring to FIG. 3, the wafer fixture 28 is formed in a conventional configuration, as is well known in the art, to immobilize the wafer 12 in a controllable position. Means are typically provided to adjust the tilt of the wafer such that the Bragg condition may be quickly satisfied with respect to the energy beam Xo. Of course, satisfying the Bragg condition may be accomplished by adjusting the energy beam, the wafer fixture position, or both.

One illustrative embodiment of a beam detector device 30 in accordance with my invention is depiction in FIG. 4. The optical detector device 30 is disposed substantially opposite the respective energy beam and optical beam sources 22 and 26 to detect the diffracted and reflected beams X' and O' from the wafer 12. The device includes, generally, a multi-axis platform 32, a circular track scale 46, and a multi-detector mechanism 56 to efficiently and accurately determine, from the detected beams, the magnitude and sense of orientation of the surface 14 of the substrate 12 with respect to the planes 16.

With particular reference to FIG. 4, the multi-axis platform 32 includes an elongated rectangularly formed base 34 having a reduced cross-sectional bridge 36 extending along a horizontal axis. The bridge slidably carries an adjustable support 38 having a clamping element 40. This bridge 36 is formed with an upwardly projecting hollow cylindrical riser 42 defining a vertical axis. The riser includes a distal open end 43 opening upwardly to telescopically receive a cylindrical extender 50 attached to the circular scale 46. An adjustable fastener 44 selectively immobilizes the arm in place to enable vertical and rotational positioning of the scale.

The scale 46 comprises a formed circular ring 48 vertically carried by the extender 50 and includes a plurality of spaced apart graduations 52 disposed around the ring for measuring angular displacement. The ring 48 defines a narrow circularly shaped band or track 47 disposed about a central reference point for guiding the multi-detector mechanism 56 therearound.

With continued reference to FIG. 4, the multi-detector mechanism 56 includes a narrow bar 58 having an adjustment end formed with a guide 60 to slidably engage the circular track 47 of ring 48. The bar includes an alignment end 62 disposed radially inwardly from the track to align with a central reference point. The alignment end mounts a fixed X-ray beam detector 64 to sense a diffracted X-ray beam X' according to one embodiment of the present invention. The bar slidably carries an optical beam detector 66 and includes a plurality of formed graduations 68 for measuring the displacement between the X-ray beam detector 64 and the optical beam detector 66.

Operation of the system and apparatus of the present invention is best described with reference to one embodiment of the method of the present invention, shown in FIG. 5.

Figure 5:
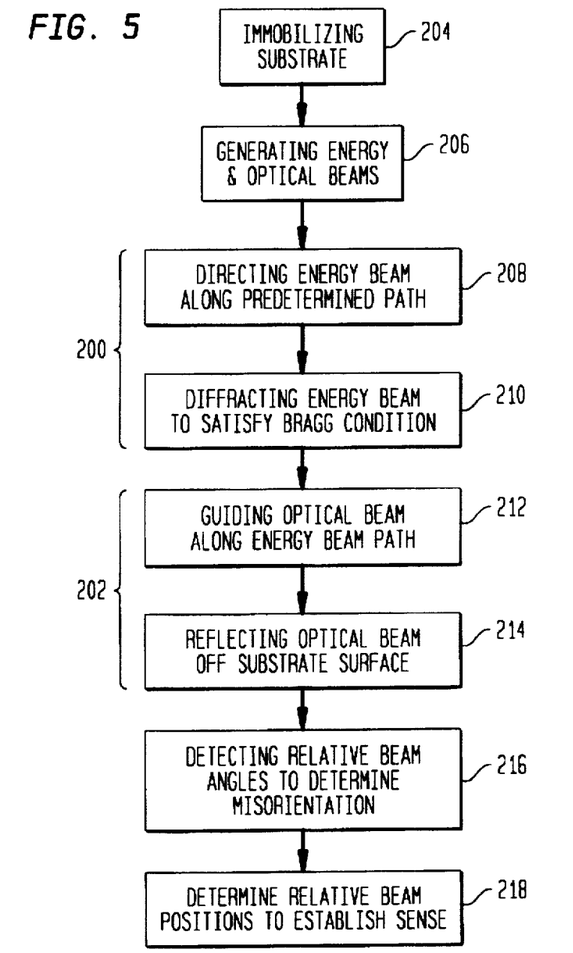
FIG. 5 is a block diagram showing steps according to one embodiment of the method of the present invention.

Implementing these general physical concepts, the method of the present invention includes establishing the reference beam of radiation Xo along a predetermined path to diffract from the near-surface crystalline planes of the wafer, at step 200 as shown in FIG. 5, and guiding an optical beam O along the predetermined path to reflect from the polished surface 14, at step 202. The relationship between the resulting diffracted and reflected beams represents the polished surface misorientation magnitude and sense.

More particularly, and further referring to FIG. 5, the method begins by first immobilizing the substrate 12, at step 204, such that the polished surface 14 is exposed and can be easily targeted by the energy beam Xo and the optical beam O. In accordance with the system of the present invention 20, this step may be conveniently carried out by mounting the substrate in the substrate fixture 28.

Following immobilization of the substrate, the respective energy and optical beams Xo and O are generated at step 206. The generated energy beam is then directed along a predetermined path, at step 208, toward the substrate surface 14. The X-ray beam, because of its nature, passes through the polished surface 14 and continues through to one of the set of underlying crystalline planes 16 (FIG. 2A), where the beam is diffracted at step 210 because the planes satisfy the Bragg condition. In satisfying the Bragg condition, the angle of diffraction matches the angle of incidence with respect to the crystalline planes, and thus serves as a convenient reference marker for the crystalline plane orientation.

To take advantage of the reference marker represented by the diffracted energy beam X', the method continues, at step 212, by guiding the optical beam along the predetermined path followed by the energy beam Xo. The optical beam O reflects off the substrate surface at a reflection angle equivalent to the angle of incidence, at step 214, to define the reflection beam O'. The resulting reflection beam serves as a measurable quantity to gauge the relative orientation of the polished surface 14 with respect to the crystalline planes 16.

The surface misorientation is then determined by detecting the respective diffracted and reflected beams and the relative angular relationship therebetween, at step 216. To identify the sense of misorientation, the relative beam positions are determined, at step 218.

Figure 6:
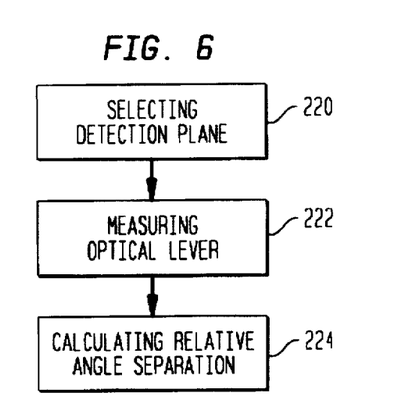
FIG. 6 is a block diagram showing the detecting step of FIG. 5 according to one embodiment of the method of the present invention.

Referring now to FIGS. 4 and 6, the detecting and determining steps, 216 and 218, are conveniently carried out by implementing the beam detection device 30, according to one embodiment of the apparatus of the present invention. As shown in FIG. 3, the detection device is disposed substantially opposite the respective energy and optical beam sources 22 and 26 to define a detection plane, at step 220 (FIG. 6). This detection plane is located a measurable distance from the substrate and is arranged to intersect the diffracted and reflected wavefronts, or beams X' and O'. The measurable distance that defines an optical lever R is measured at step 222 and is used to calculate the misorientation, step 224.

Figure 2:
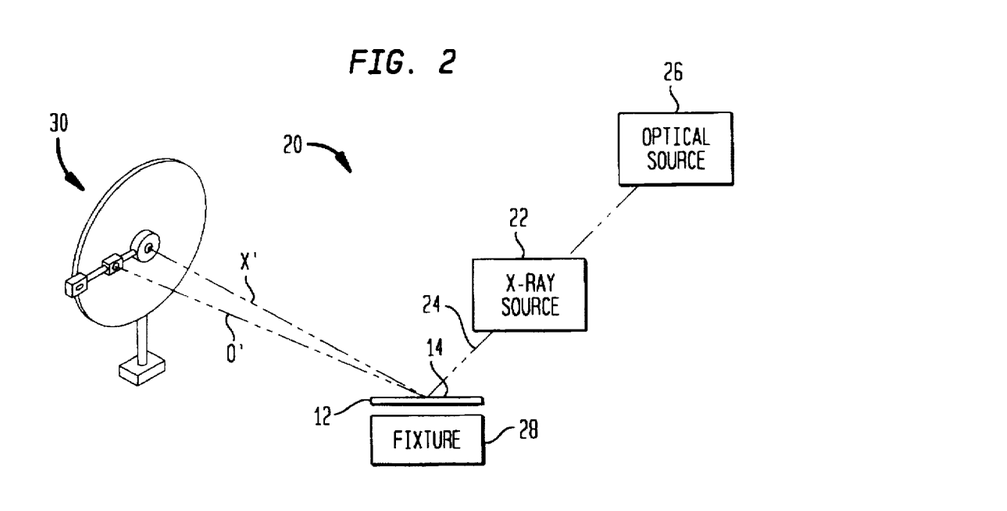
FIG. 2A is an enlarged partial cross-sectional side view of a wafer similar to that shown in FIG. 1B, and illustrating the physical concepts involved in the present invention.
FIG. 2B is an enlarged partial cross-sectional side view similar to FIG. 2A.

Once positioned, the circular scale 46 of the device 30, FIG. 4, is adjusted to align the x-ray beam detector 64 with the diffracted energy beam X', and the multi-detector mechanism bar 58 is placed substantially perpendicular to the diffracted beam path, as shown in FIG. 2. The bar is then rotated along the track 48, and the optical beam detector 66 then slid along the bar 58 until aligned with the reflected optical beam O'. The relative spacing between the detected beams may be easily identified by the spaced apart graduations 68 so as to represent the quantity $\Delta X$. This quantity is then used with the optical lever, R, to calculate the relative angular separation, or misorientation $\theta$, according to the equation:

$$\theta = \Delta X / 2R$$

Moreover, by merely noting the relative position of the respective diffracted and reflected beams X' and O', as indicated by the angular position of the multi-detector mechanism 56 along the scale track 54, one may easily determine the sense of misorientation.

While the steps above have been described with reference to using the aforedescribed multi-detector mechanism 56, it is anticipated that a flat or spherical scale may be used that eliminates the detectors 64 and 66, and instead includes a readable surface such that the relative angular spacing of the beams X' and O' may be visually determined through, for instance, visual inspection.

Figure 7:
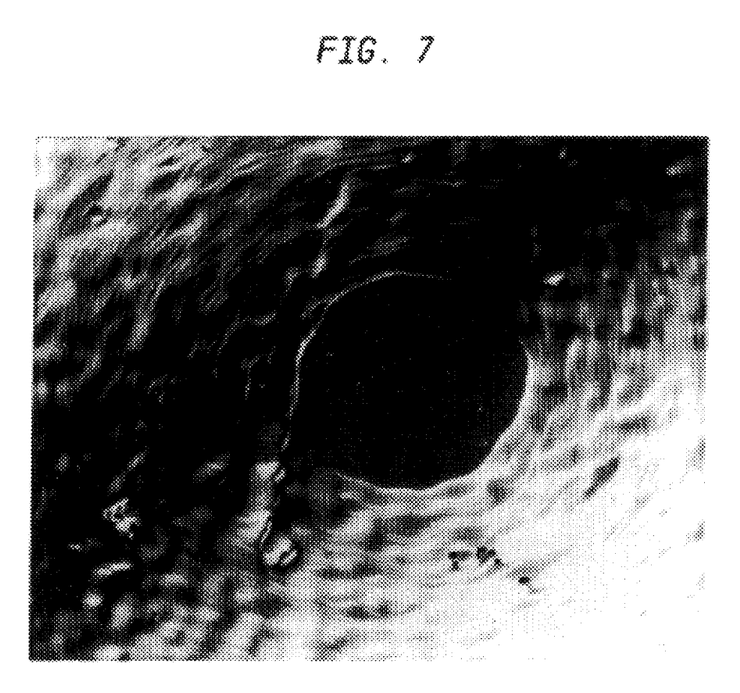
FIG. 7 is a photograph of an enlarged top plan view of the effects of misorientation on an InP layer grown on an InP substrate having a spherical surface ground on it.

As noted previously, the failure to fully screen wafers according to the magnitude and sense of misorientation raises the potential for unnecessary waste and costs due to defects which form during subsequent processing operations because the misorientation is incorrect. For example, FIG. 7 is a photograph showing the effect of surface misorientation on the quality of an InP layer grown by liquid phase epitaxy on an InP substrate having a formed spherical surface. The exact (100) surface orientation produced a highly flat facet (the central planar area), whereas the terraced growth occurred at the misoriented surface all around it.

Those skilled in the art will appreciate the elegant straightforwardness of the detection apparatus and measuring method described above for the many advantages afforded. Especially significant is the minimal time required to make the misorientation measurement. For this reason alone, the apparatus and method of the present invention readily lend themselves to high production semiconductor processing operations. By having the capability of screening wafers in a high production environment during the early stages of device fabrication, substantial reductions in the number of defective devices may be realized resulting in corresponding reductions in cost.

Additionally advantageous is the non-destructive nature of the invention which further minimizes costs by eliminating any additional etching processes and chemicals. This allows measurements of actual production wafers which dramatically reduces unknown variables typically associated with defective wafers set aside for destructive testing purposes.

The improved accuracy and repeatability of the invention will also be appreciated by those skilled in the art. These features are realized because of the "direct" measurement approach utilized by the invention, which eliminates any interpreting steps characteristic of indirect methods.

The process may in most respects be automated if the fixture adjustments are automated and the motions of support 38, riser 42 and guide 60 are achieved, e.g. by stepper motors under the control of a computer operated according to a program as set forth in the flow charts of FIGS. 5 and 6.

While the invention has been particularly shown and described with reference to the preferred embodiments thereof, it will be understood by those skilled in the art that various changes in form and detail may be made therein without departing from the spirit and scope of the invention.

What is claimed is:

1. A method for identifying the misorientation of a polished surface of an immobilized monocrystalline substrate with respect to a set of low index crystalline planes aligned in parallel relationship and formed beneath said surface, said method including the steps of:

establishing a reference beam along a predetermined path to non-destructively penetrate said surface and diffract from said set of planes at a predictable angle to define a diffraction beam;

guiding an optical beam along said predetermined path collinear with said reference beam to reflect from said misoriented surface of said substrate and define a reflected beam ; and determining a relative separation and position of said reflected beam from said diffraction beam, said relative separation and position representing the magnitude and sense of the misorientation between said polished surface and said crystal planes.

2. A method according to claim 1 and further including the step of:

comparing the separation between said diffraction beam and said reflected beam to determine the magnitude of said misorientation.

3. A method according to claim 1 and further including the step of:

determining the relative position of said reflected beam to said diffracted beam to establish a sense of said misorientation.

4. A method according to claim 1 wherein said establishing step includes:

generating said reference beam; and directing said reference beam along said predetermined path to penetrate said polished surface and intersect at least one of said crystal planes at an angle of incidence such that said reference beam diffracts from said planes at a diffraction angle equivalent to said angle of incidence.

5. A method according to claim 4 wherein said directing step includes:

positioning said substrate with respect to said reference beam so said crystal planes satisfy the Bragg condition.

6. A method according to claim 5 further including the step of comparing the separation between said diffraction beam and said reflected beam to determine the magnitude of said misorientation as an angular separation between said diffraction beam and said reflector beam, said misorientation being one half of the angular separation.

7. A system for measuring the misorientation of the polished surface of a monocrystalline substrate with respect to a vicinal low index crystal plane formed in said substrate, said system comprising:

means for generating and directing a reference beam along a path to a point on the surface of said substrate, through said surface to the crystal plane located below said surface, and diffracted away from said crystal plane;

means for generating and directing an optical beam collinear with the path of said reference beam so as to impinge on said point on the surface of said substrate and be reflected therefrom;

means for receiving the optical beam reflected from said substrate;

means for receiving the reference beam diffracted from the crystalline plane; and means for determining the angle between said reflected and diffracted beams.

8. A system as claimed in claim 7 wherein said means for generating and directing said reference beam is an X-ray source and said means for generating and directing said optical beam is a light source.

9. A system as claimed in claim 8 wherein said light source is one of a visible, infrared and ultraviolet light source.

10. A system as claimed in claim 9 wherein said means for receiving the optical beam is a light beam detector and said means for receiving the reference beam is an X-ray detector.

11. A system as claimed in claim 10 wherein said means for determining comprises;

a multi-axis platform;

a scale mounted to said platform and having an adjustment track, said track formed along a track path disposed radially equidistant from a predetermined point; and a detector support adjustably mounted to said track and supporting said light detector and X-ray detector in measurably adjustable relative relation on said mechanism in order to determine angular separation between reflected optical and diffracted energy beams from said substrate.

12. A detection device for use with a measurement system for measuring the misorientation of a monocrystalline substrate surface, said system having a reference beam and an optical beam source collinearly directed to a substrate, and reflected and diffracted beams for subsequent detection, said detection device comprising:

a multi-axis platform for providing adjustable support in multiple directions;

a scale mounted to said platform and having an adjustment track, said track formed along a track path disposed radially equidistant from a predetermined point;

a multi-detector mechanism mounted on said scale and including respective reference beam and optical beam detectors disposed in measurably adjustable relative relation, one of said detectors of said detection device being at said predetermined point and the other being located on a bar extending from said predetermined point to the track of said scale, said bar being adjustable along said track and said other detector being adjustable along said bar so said detectors align with said diffracted and reflected beams and define a relative spacing therebetween representing the sense and magnitude of misorientation of said polished surface with respect to a vicinal low index crystal plane.

13. A detection device according to claim 12 wherein said platform includes:

a rectangularly formed horizontal base;

an upwardly projecting riser mounted slidably on said base along a first axis, said riser including an arm telescopically extendable from the distal end of said riser along a second axis perpendicular to said first axis.

14. A detection device according to claim 13 wherein:

said scale is formed with a circular ring having a central point at said predetermined point and mounted upright to a distal end of said arm, said ring being formed with a plurality of calibrated graduations for measuring angular displacement, said ring defining said track path; and said central point defining said predetermined point.

15. A detection device according to claim 12 wherein:

the bar of said multi-detector mechanism includes an outer end mounted slidably to said track such that said bar projects radially inwardly toward the center of said ring, said bar being formed with displacement indicators for determining distance along said bar;

said reference beam source is an X-ray source and said one detector is an X-ray detector disposed at said predetermined point toward the opposite end of said bar for aligning with said diffracted beam; and said optical beam source is a light source and said other detector is an optical detector mounted slidably on said bar for aligning with said reflected beam.

16. A misorientation system for measuring the misorientation of the polished surface of a monocrystalline substrate with respect to a vicinal low index crystal plane formed in said substrate, said system comprising:

a reference beam source for generating an energy beam;

an optical beam source for generating an optical beam collinear with said reference beam;

a substrate fixture disposed in-line with said reference beam and said optical beam for immobilizing said substrate in an adjusted position; and a detection device including:

a multi-axis platform for providing adjustable support in multiple directions;

a scale mounted to said platform and having an adjustment track, said track formed along a track path disposed radially equidistant from a predetermined point; and a multi-detector mechanism mounted adjustably to said track and including respective reference beam and light beam detectors disposed in measurably adjustable relative relation on said mechanism to determine angular separation between said reflected optical and diffracted reference beams from said substrate.

17. A misorientation system according to claim 16 wherein said reference beam source comprises an X-ray generator for producing an X-ray beam.

18. A misorientation system according to claim 16 wherein said optical beam source comprises a visible light source for producing a visible light beam.

19. A misorientation system according to claim 16 wherein said optical beam source produces one of an infrared light and ultraviolet light beams.

20. A method for measuring the misorientation of a polished surface of a substrate with respect to a set of low index crystal planes aligned in parallel relationship and formed beneath said polished surface, said method including the steps of:

generating respective reference and optical beams;

directing said reference beam along a predetermined path to penetrate said polished surface of said substrate and intersect at least one of said crystal planes of said substrate at an angle of incidence such that said reference beam diffracts from said set of planes at a diffraction angle equivalent to said angle of incidence;

guiding said optical beam along said predetermined path collinear with said reference beam to intersect said polished surface such that said optical beam reflects from said surface at a reflection angle to define a reflected beam; and detecting the relative angle between said diffraction angle and said reflection angle to identify the misorientation of said polished surface.

21. A method according to claim 20 and further including the step of:

determining the relative positions of said reflected beam and said diffracted beam to establish a sense of said misorientation.

22. A method according to claim 20 wherein said generating step includes:

generating an X-ray beam and a visible light beam.

23. A method according to claim 20 wherein said directing step includes:

positioning said substrate with respect to said predetermined path such that said crystal planes satisfy the Bragg condition.

24. A method according to claim 20 wherein said detecting step includes the steps of:
   selecting a detection plane disposed a distance from said structure and substantially perpendicular to said reflected beam;
   measuring said distance to define an optical lever R;
   identifying the relative separation $\Delta X$ along said detection plane between said reflected beam and said diffracted beam; and
   calculating the misorientation of said substrate by dividing $\Delta X$ by 2R.

25. A method according to claim 20 wherein said detecting step utilizes a beam detection device having a multi-axis platform for providing adjustable support in multiple directions, a scale mounted to said platform and having an adjustment track, said track formed along a track path disposed radially equidistant from a predetermined point, and a multidetector mechanism mounted adjustably to said track and including respective reference beam and light beam detectors disposed in measurably adjustable relative relation along said mechanism and comprising the steps of:
   positioning said detection device a measurable distance from said point of incidence of said reflected optical beam to define an optical lever;
   aligning said reference beam detector to a position on said scale to sense said diffracted beam, and aligning said optical detector to a position on said scale to sense said reflected optical beam, the relative positions of said detectors defining a detection plane disposed a distance from said substrate corresponding to said optical lever;
   calculating with said scale the relative separation along said detection plane between said reflected beam and said diffracted beam to measure said misorientation; and
   determining the relative positions of said aligned and positioned detectors to measure said sense of misorientation.

26. A method for measuring the misorientation of a polished surface of a monocrystalline substrate with respect to a set of low index crystal planes formed beneath said polished surface, said method for use with a measurement system including an X-ray beam source, a visible light beam source, and a beam detection device, said method including the steps of:
   generating respective X-ray and visible light beams with said X-ray beam and light beam sources;
   directing said X-ray beam along a predetermined path to penetrate said polished surface and intersect said set of crystal planes at an angle of incidence sufficient to satisfy the Bragg condition;
   guiding said light beam along said predetermined path co-linear with said X-ray beam to intersect said polished surface such that said light beam reflects from said surface at a reflection angle to define a reflected beam;
   detecting the relative angle between said diffraction angle and said reflection angle with said beam detection device to identify the misorientation of said polished surface; and
   determining the relative position of said reflected beam and said diffracted beam with said beam detection device to establish a sense of said misorientation.

* * * * *